United States Patent [19]

Traina et al.

[11] Patent Number: 5,520,048
[45] Date of Patent: May 28, 1996

[54] AUTOMATED FLOW MEASURING DEVICE INCLUDING WET AND DRY BULB MOISTURE ANALYZER

[75] Inventors: John E. Traina, Glenshaw; Richard Myers, Gibsonia, both of Pa.

[73] Assignee: United Sciences, Inc., Gibsonia, Pa.

[21] Appl. No.: 375,527

[22] Filed: Oct. 19, 1995

[51] Int. Cl.⁶ .............................. G01N 25/62; G01F 1/42
[52] U.S. Cl. ................. 73/335.060; 73/861.650; 73/29.020; 374/148.000
[58] Field of Search .......................... 73/335.06, 861.65, 73/29.02, 29.01

[56] References Cited

U.S. PATENT DOCUMENTS

| | | | |
|---|---|---|---|
| 2,040,771 | 5/1936 | Heyroth | 73/24 |
| 2,128,176 | 8/1938 | Bast et al. | 236/44 |
| 2,623,391 | 12/1952 | Malecki | 73/338 |
| 2,706,409 | 4/1955 | Preston | 73/212 |
| 2,845,790 | 8/1958 | Eddy | 73/29 |
| 3,911,183 | 10/1975 | Hinkes | 428/15 |
| 3,977,249 | 8/1976 | Wittig | 73/212 |
| 4,222,261 | 9/1980 | Leblanc et al. | 73/29 |
| 4,343,194 | 8/1982 | Dehart et al. | 73/861.65 |
| 4,476,729 | 10/1984 | Stables et al. | 73/861.61 |
| 4,717,159 | 1/1988 | Alston et al. | 277/1 |
| 5,148,710 | 9/1992 | Gudehus et al. | 73/335.06 |
| 5,394,759 | 3/1995 | Traina | 73/861 |

FOREIGN PATENT DOCUMENTS 2231667  11/1990  United Kingdom .

OTHER PUBLICATIONS

Technisches MEssen Tm, vol. 48, No. 6, Jun. 1981, Munchen De, pp. 229–232, J. Wachter, A. Heneka und K. Schweizer "Automatischer Nullabneich fur Stromungs-sonden".

Appendix A, Title 40, United States Code of Federal Procedure, Part 60, Chapter 1, EPA Methods 1 and 2, pp. 481–509, Jul. 1, 1993.

Primary Examiner—Hezron E. Williams
Assistant Examiner—J. David Wiggins
Attorney, Agent, or Firm—Buchanan Ingersoll; Lynn J. Alstadt

[57] ABSTRACT

An improved probe useful for measuring emissions of stack gases is equipped with a means for measuring moisture content and molecular weight of stack gases. A water feed tube is provided through the distal end of the probe and is fed water via a water feed line. An electrical temperature measuring device and water soaker device having spaced apart soaker feed holes is provided near the distal end of the water feed tube while a dry tubing encases the water feed tube below the temperature measuring device. A soaker wick encases part of the water feed tube and covers all of the temperature measuring device. Finally, an internal seal is provided between the dry tubing and the temperature measuring device to prevent thermally conductive heat from reaching the temperature measuring device. This structure enables the probe to make wet bulb-dry bulb measurements of stack gases.

4 Claims, 4 Drawing Sheets

AUTOMATED FLOW MEASURING DEVICE INCLUDING WET AND DRY BULB MOISTURE ANALYZER

FIELD OF INVENTION

The invention relates to a probe used to measure stack gas velocity, volumetric flow rate and moisture content which is useful for emissions monitoring.

BACKGROUND OF THE INVENTION

The federal government of the United States has promulgated test methods in 40 CFR Part 60, Appendix A for determining stack gas velocity, volumetric flow rate and moisture content. If one knows the flow rate and has another monitor which measures the concentration of pollutants in a selected volume of fluid one can calculate the quantity of pollutants emitted over any selected time period. Accordingly, the test methods have been used in various ways, including the verification of the performance of continuous emission monitoring equipment required by other rules.

The United States has additional regulatory requirements in the form of 40 CFR, Parts 72 through 75 (acid rain reduction), which utilize the Appendix A methods. Some recent regulations now require many electric utilities to continuously measure emissions of specified pollutants on a mass per unit time basis. Adoption of these rules has put a new importance on the errors in both the continuous monitor and in the referenced test methods. The new regulations establish monetary value in the form of trading credits to a ton of $SO_2$ emissions. The value of such emissions is such that for large utilities as much as $1,000,000 per percent error in measured emissions may result.

The methods of Appendix A were introduced into law over 20 years ago. They, in general, use simple laboratory apparatus and manual techniques to make the various measurements. Unfortunately, the methods are error prone and tests under the same conditions often yield different results. There are many sources of error related to the care, speed and experience of the personnel performing the method as well as variability of the test hardware itself. Over the years, the need to reduce the errors in these methods have been the subject of much discussion and little action.

Appendix A of Title 40 of the United States Code of Federal Regulations contains two methods for measuring flow which are used to determine compliance with emission regulations. These methods, known as EPA Methods 1 and 2, have gained prominence because they are used to determine the proper location, as well as to verify the performance of continuous measuring flow monitors. Errors in Method 2 data can be very costly to both the supplier of the monitor and the utility. The supplier is affected because the method can erroneously show the monitor is not meeting the performance guarantee. The utility is affected because the method is used to adjust the continuous monitor. If the method is in error, that error will directly cause an enormous high or low use of the utility's $SO_2$ allowance and $SO_2$ trading credits.

Our United States patent application Ser. No. 08/238,262, filed May 4, 1994, discloses an automated probe for measuring velocity and flow rate of stack gases. The probe is made and sold by United Sciences, Inc. under the trademark AUTOPROBE 2000. However, prior to the present invention this device was not able to determine the moisture content of stack gases.

The equation for calculating flow velocity from the delta-pressure of a pitot tube contains the molecular weight of the gas being measured. In performing the required testing methods the technician is therefore required to determine the molecular weight of the stack gases being monitored. This determination includes measuring moisture content of the stack gases. Method 4 of Appendix A of Title 40 of the United States Code of Federal Regulations describes two procedures for determining moisture content in stack gases and goes on to say that alternative means for approximating the moisture content including use of wet bulb-dry bulb temperature techniques are acceptable. Determination of the stack gas moisture concentration of water vapor by the procedures described in Method 4 are cumbersome. Similarly, the wet bulb-dry bulb techniques which have been used in the past are also cumbersome insomuch as their operation was manual and the data interpretation, consisting of identifying the wet-bulb temperature, reading a psychometric chart and performing barometric compensation was also manual.

There is a need for an accurate and convenient method and apparatus for measuring moisture content of stack gases which can be used for emissions monitoring. Moreover, the apparatus must be durable and not adversely affected by temperature changes and other environmental conditions found in power plants and other monitoring sites.

SUMMARY OF THE INVENTION

According to the present invention a retractable probe is equipped with a means for measuring moisture content of stack gases. A water feed line is provided through the distal end of the probe. A platinum resistance temperature detector (RTD) or other suitable device for measuring temperature is located within a tube having spaced apart soaker feed holes. A water feed tube is provided on the distal end of the feed line while a dry tubing encases the perforated end of the tube containing the water feed line below the RTD. A soaker wick encases the RTD and extends over at least a portion of the outer tube. Finally, an internal seal is provided between the portion within which water is supplied to the RTD and the portion which is desired to be dry. This structure enables the probe to make wet bulb-dry bulb measurements of stack gases using a single RTD or other temperature measuring device.

Other details, objects and advantages of the present invention will become apparent from the description of the preferred embodiment shown in the drawings.

DESCRIPTION OF THE PREFERRED EMBODIMENTS

Figure 1:
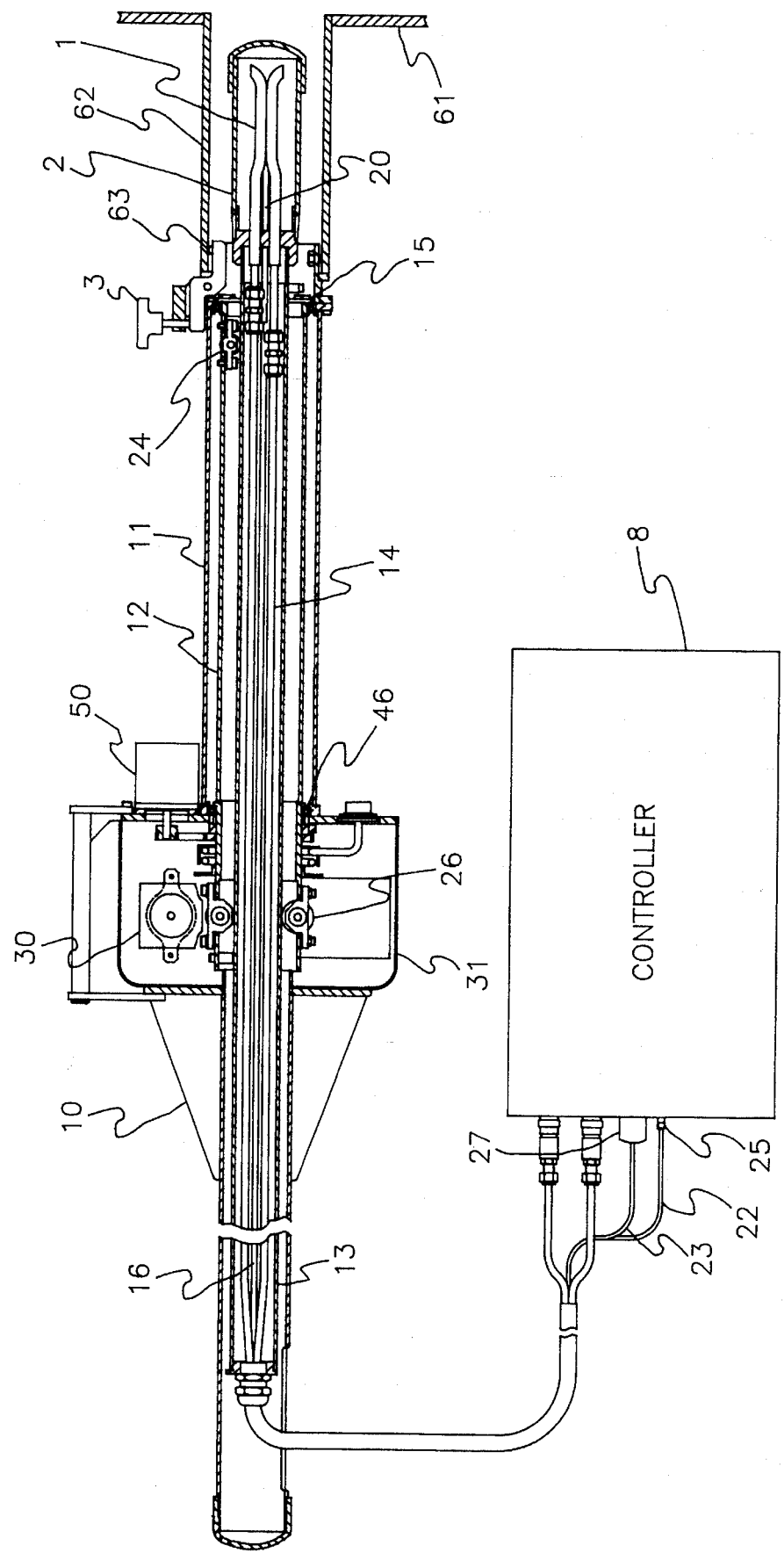
FIG. 1 is a side view partially in section of a present preferred probe assembly including the means for measuring moisture content of stack gases.

The present preferred probe to which the moisture measuring structure is attached is disclosed in detail in United States patent application Ser. No. 08/238,262, filed May 4, 1994. The basic configuration of that probe is shown in FIG. 1. Further details of that probe and its method of operation may be found in that patent application the contents of which are hereby incorporated by reference.

Referring to FIG. 1, the preferred probe assembly 10 contains an outer tubular housing 11, middle tubular housing 12 and an inner tubular housing 13, all made of corrosion resistant metal. Two sample conduits 14 run through the housing 13. A pitot tube 1 is attached to the end of the conduits 14. A removable cover 2 fits over the pitot tube 1. We prefer to use a four foot conduit 14, but other lengths up to 12 feet are acceptable. A third conduit 16 is preferably provided containing a temperature probe and the means for measuring moisture content shown in FIG. 2. A clamp assembly 3 with cone pointed set screw 63 and seal 15 allow the probe assembly 10 to be mounted in a port 62 on a stack or duct 61. If desired bosses or other structures could be provided to assure that the probe assembly is always positioned in the same location when attached to the stack. Hence, tests can be repeated over time with the assurance that data is always being collected from the same points within the stack. The tubular inner housing rolls linearly on the roller assemblies 24 near the distal end of housing 12 and roller assemblies 26 near the drive motor 30. This housing 12 may also rotate on the bearing assemblies 46. Within the housing 31 there is a motor 30 for advancing and retracting housing 13 and a second motor 50 for rotating housing 13. Extending from the distal end of conduit 16 through cap 18 is the assembly 20 for making wet bulb-dry bulb measurements shown in detail in FIG. 2. A water feed line 22 and wires 23 extend from the assembly through conduit 16 to connectors 25 and 27. The motors and wet bulb-dry bulb device are connected to a controller 8 which controls water flow into the wet bulb-dry bulb device, controls movement of the probe, receives differential pressure reading made through the pitot tube, and determines molecular weight of the gases in the conduit. This controller enables the automated determination of molecular weight of the gases.

The science of wet bulb-dry bulb hygrometry is based on the fact that, when a film of water is exposed to a moving stream of gas, an equilibrium evolves such that the heat convected into the film, by the gas is exactly balanced by the heat of evaporation of water at the surface of the film, such that there is no net transfer of heat through the film. The reason that the stream of gas should be moving (typically at a speed not less than 10 ft/sec) is to ensure that the convective and evaporative heat transfer process predominate over other heat transfer processes such as radiation or conduction through the temperature measuring device. Under this equilibrium, the wet bulb temperature becomes equal to the adiabatic saturation temperature over a wide range of temperature and relative humidity. This phenomenon is applicable for combinations of water and air (or water and "air-like" gases), but does not apply to many other mixtures such as organic solvents.

Figure 2:
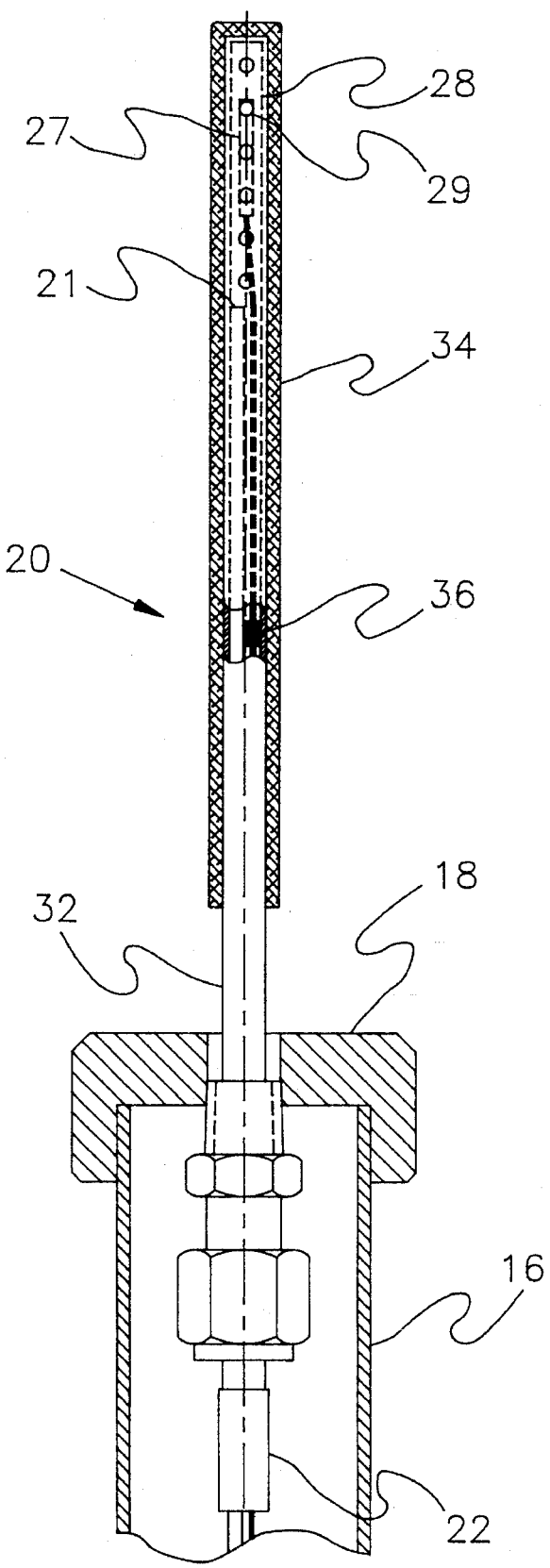
FIG. 2 is a side view partially in section showing the preferred means for measuring moisture content.

FIG. 2 shows the preferred assembly 20 for making wet bulb-dry bulb measurements. A water feed line 22 extends through conduit 16 and cap 18 to the exterior of the probe. At the distal end of the water feed line is a water feed tube 21 and soaker device 28 having a plurality of soaker holes 29. An electrical temperature sensing device such as a platinum retarding potential difference (RTD) temperature sensor device 27 or a thermistor is provided within the soaker device. A dry portion 32 of the water feed line 22 is provided below the soaker device and electrical temperature measuring device contained therein. A soaker sleeve or wick 34 encases the soaker device and extends to the dry portion 32 of the water feed line. A suitable material for the soaker sleeve is "NEXTEL" alumina-boric-silica fiber, available from McMaster-Carr. An internal seal 36 is provided between the soaker wick and dry portion of the water feed line. Deionized water is fed through line 22 and tube 21 into the soaker 28 in such a way as to saturate the soaker sleeve or wick 34 that covers the RTD device 27. The soaker sleeve 34 extends considerably down the assembly 20 from the RTD element 27 so that the heat conduction from the "dry" section of the probe 32 is removed by evaporating cooling of the water on the wet soaker sleeve or wick and cannot reach the RTD device. This same geometry also swamps out any effect of the heat carried by the water itself. With an appropriate water feed rate, the convective/evaporative effects solely determine the equilibrium temperature at the tip of the probe where the RTD is located. When the water feed is terminated, the "dry" portion of the probe sends heat via conduction into the sleeved section and speeds up the return to dry equilibrium condition that determines the dry-bulb temperature.

Figure 3:
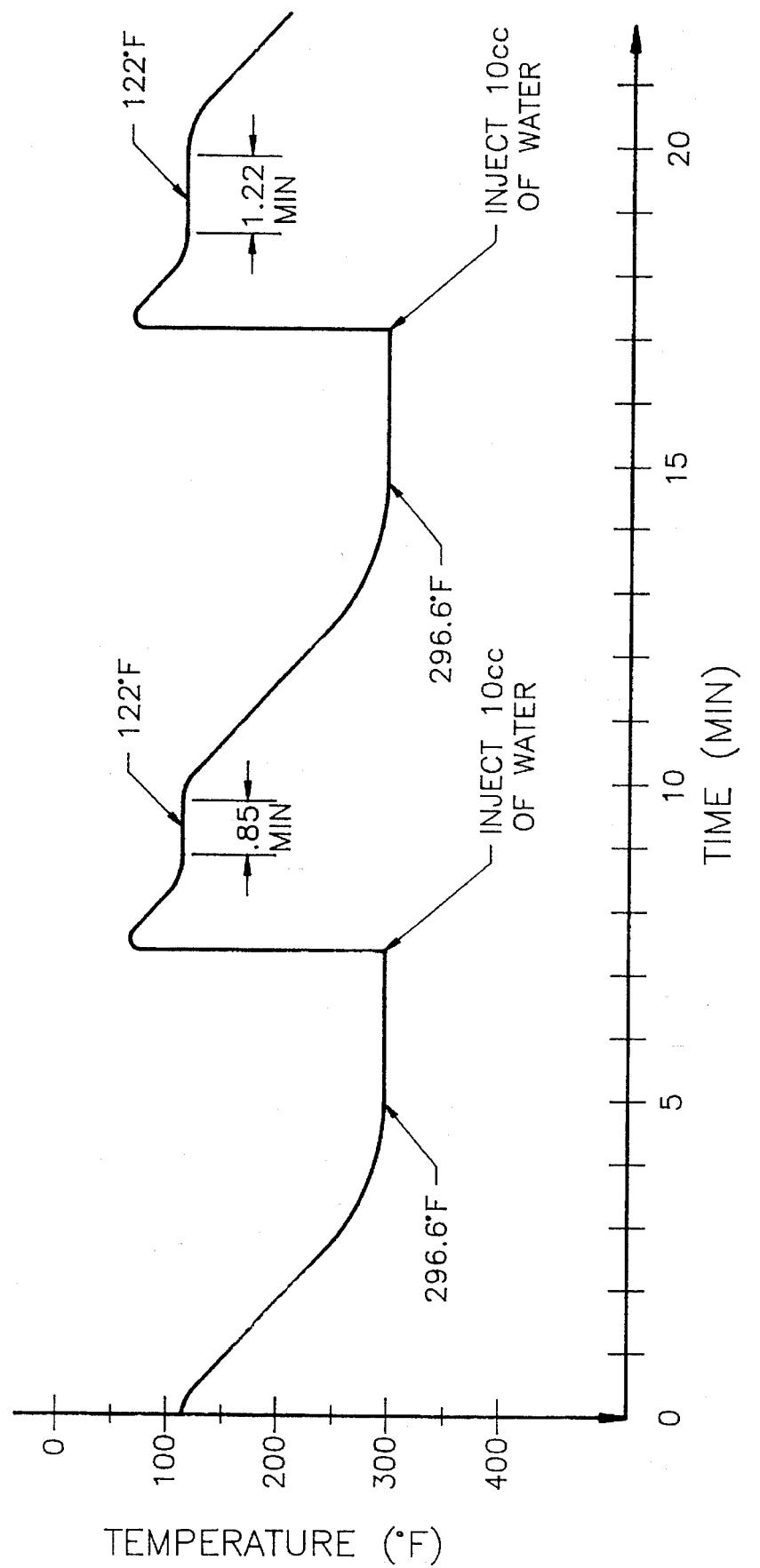
FIG. 3 is a chart showing the results of testing in an operating stack.

FIG. 3 shows results of testing on an operating stack of a coal-burning electric utility with flow velocity about 50 ft/sec and dry-bulb temperature about 300 degrees F. The vertical (elapsed time) chart calibration is 0.75 min./cm. Relevant temperature and elapsed times are written on the chart. Although only two cycles of testing are shown, about ten cycles were actually repeated, with identical results. In addition, a number of tests have been run on a laboratory simulation apparatus.

When the water is injected into the soaker sleeve quickly, the wet-bulb temperature may, depending on the stack and ambient conditions, fall below the "true" value. However, if the soaker contains sufficient water for the equilibrium to be established before the soaker sleeve begins to dry out, a wet-bulb equilibrium will always be established. It is important to note that just after water has been injected, and once the sleeve beings to dry out, the x-axis values are not stable. Only during the dry condition and during the (approximate 1 minute) period of wet-bulb stability is the RTD temperature measurement stable.

Based on tests to date, one strategy (out of a number of possibilities) for reading the wet-bulb $T_w$ and dry-bulb $T_d$ temperature is to first read the dry temperature at least ten minutes after any water has been injected. Then, inject 10 cc of deionized water over a period of several seconds. Monitor the rate of change of $T_w$ as well as $T_w$ itself. Wait until the rate of change of $T_w$ is less than 0.01 degrees F./sec. over a period of at least 10 seconds. Then, record $T_w$ as the temperature associated with the lowest rate of change (i.e. most stable) of $T_w$ prior to a 5 degree F. temperature increase from the most stable $T_w$. The 5 degree F. temperature rise may be taken as evidence that the soaker sleeve has begun to dry out.

Figure 4:
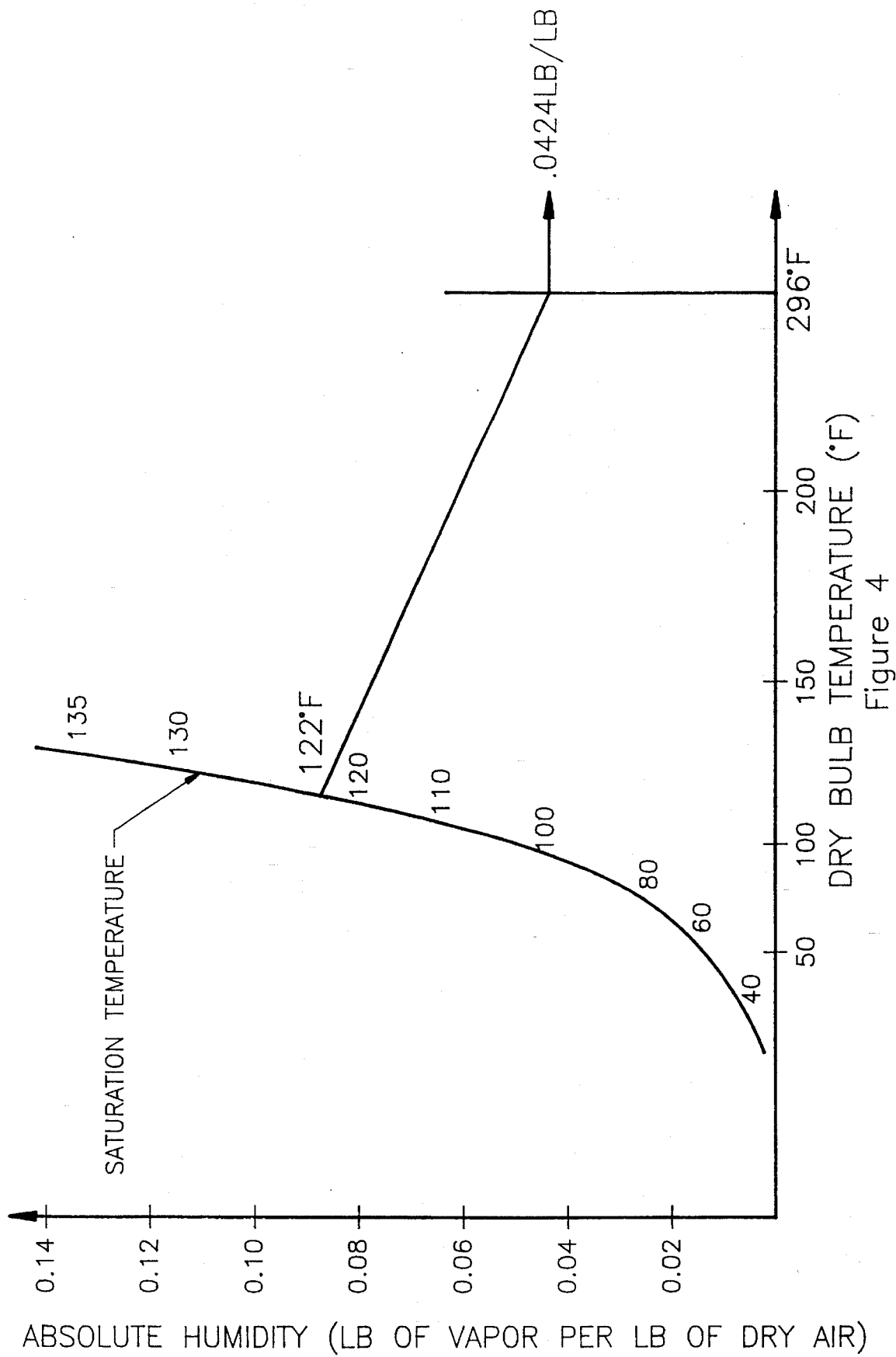
FIG. 4 is a psychometric chart on which certain test data is noted.

FIG. 4 shows a high-temperature psychometric chart. The first step of using this chart is to locate the wet-bulb temperature $T_w$ on the ascending left-hand curve. The next step is using the chart to follow the downward-sloping line from $T_w$ to a point vertically above the dry bulb temperature. From here, one can read horizontally across to the Absolute Humidity $H_a$. This process is shown for the wet bulb-dry bulb data shown in FIG. 3, yielding $H_a$=0.0424 of water vapor per pound of dry flue gas.

$H_a$ is the absolute humidity at a nominal barometric pressure of 760 mmHg. The barometrically corrected absolute humidity $H_{bc}$ is given by:

$$H_{bc} = H_a + (.622)(p_w)\left[\frac{1}{p-p_w} - \frac{1}{760-p_w}\right]$$

where $p_w$ is the vapor pressure of water at $T_w$ (92.51 mm Hg in our example)

P is the measured absolute barometric pressure (measured by at 748 mm Hg in our example).

This gives the mass of water per mass of dry air for our example of:

$$H_{bc} = 0.0424 + (.622)(92.51)\left[\frac{1}{748-92.51} - \frac{1}{760.92.51}\right] =$$

0.04398 (a significant correction).

The percent water by volume on a wet basis (using a value of 29 for molecular weight of the flue gas) is:

% $H_2O = (1.6111 \; H_{bc}) \div (1+1.611 \; H_{bc}) = 0.0666$ or 6.6% of moisture by volume.

In the implementation of the wet bulb-dry bulb determination of stack moisture for determination of molecular weight, all of the calculations, including digitization of the high-temperature psychometric chart has been incorporated into the computer which controls the probe, along with the inputs of $CO_2$ and/or $O_2$ from the certified continuous emissions monitor. The result is an automated device that can directly implement the equation for calculating flow velocity without the need for any ice baths, impingers, Orsats, or other extractive apparatus.

Although we have described and shown certain present preferred embodiments of our invention, it should be distinctly understood that the invention is not limited thereto, but may be variously embodied within the scope of the following claims.

We claim:

1. An improved probe for analyzing stack gas flow of the type having a pitot tube which is used to measure velocity of gases moving through a stack into which a distal end of the probe is inserted through a port, duct or aperture thereon, and oriented relative to flow of gas within the stack wherein the improvement comprises a wet bulb-dry bulb temperature device for measuring moisture content of stack gases flowing past the pitot tube with the wet bulb-dry bulb temperature device being attached to the probe adjacent the pitot tube.

2. The improved probe of claim 1 wherein the wet bulb-dry bulb device for measuring the content of stack gases comprises:

a. a water feed tube extending through the distal end of the probe and having a distal end and a dry portion spaced apart from the distal end;

b. a water feed line which supplies water to a water feed tube;

c. a water soaker having a plurality of soaker holes, and connected to the distal end of the water feed tube such that water flowing through the water feed tube will be emitted through the water soaker holes of the soaker:

d. an electrical temperature measuring device positioned near the distal end of the feed tube and suitable for connection to at least one of a display, gauge and instrument set located outside of the stack;

e. a soaker wick disposed to cover part of the water feed tube, providing a wet portion of water feed tube and encasing the water soaker and at least part of the electrical temperature sensing device to form a wet bulb environment exposed to a gas flow; and f. an internal seal positioned between the dry portion of the water feed tube and the wet portion of the water feed tube, where the wet portion of said water feed tube includes the soaker wick, water soaker and electrical temperature sensing device.

3. The improved probe of claim 2 wherein the electrical temperature sensing device is one of a retarding potential difference temperature sensor and a thermistor.

4. The improved probe of claim 2 also comprising a controller having a computer and connected to the probe and the electrical temperature sensing device for automatically determining molecular weight of the gases in the conduit from a set of measurements including gas velocity, moisture content and temperature.

\* \* \* \* \*

UNITED STATES PATENT AND TRADEMARK OFFICE
CERTIFICATE OF CORRECTION

PATENT NO. : 5,520,048

DATED : May 28, 1996

INVENTOR(S) : JOHN E. TRAINA, RICHARD MYERS

It is certified that error appears in the above-indentified patent and that said Letters Patent is hereby corrected as shown below:

Title page,
At [22] Filed, change "October" to --January--.

Signed and Sealed this

Twenty-seventh Day of August, 1996

Attest:

BRUCE LEHMAN

*Attesting Officer*     *Commissioner of Patents and Trademarks*